(12) United States Patent
Myllärinen et al.

(10) Patent No.: US 9,888,699 B2
(45) Date of Patent: Feb. 13, 2018

(54) PRODUCT AND PROCESS FOR ITS PREPARATION

(75) Inventors: Päivi Myllärinen, Helsinki (FI); Kirsi Rajakari, Espoo (FI)

(73) Assignee: VALIO LTD., Helsinki (FI)

( * ) Notice: Subject to any disclaimer, the term of this patent is extended or adjusted under 35 U.S.C. 154(b) by 410 days.

(21) Appl. No.: 13/318,881

(22) PCT Filed: May 4, 2010

(86) PCT No.: PCT/FI2010/050361
§ 371 (c)(1),
(2), (4) Date: Nov. 4, 2011

(87) PCT Pub. No.: WO2010/128027
PCT Pub. Date: Nov. 11, 2010

(65) Prior Publication Data
US 2012/0058224 A1  Mar. 8, 2012

(30) Foreign Application Priority Data

May 4, 2009 (FI) ..................................... 20095500

(51) Int. Cl.
| | | |
|---|---|---|
| A23C 9/00 | (2006.01) | |
| A23C 9/14 | (2006.01) | |
| A23C 9/12 | (2006.01) | |
| A23C 9/13 | (2006.01) | |
| A23L 33/26 | (2016.01) | |

(52) U.S. Cl.
CPC .............. *A23C 9/14* (2013.01); *A23C 9/1206* (2013.01); *A23C 9/1216* (2013.01); *A23C 9/1307* (2013.01); *A23L 33/26* (2016.08); *C12Y 203/02013* (2013.01); *A23V 2002/00* (2013.01)

(58) Field of Classification Search
CPC ....... A23C 9/14; A23C 9/1206; A23C 9/1216; A23C 9/1307; A23V 2002/00; A23V 2200/3322; A23V 2200/3324; C12Y 203/02013; A23L 33/26
USPC ............ 426/34, 42, 392, 422, 424, 580, 583
See application file for complete search history.

(56) References Cited

U.S. PATENT DOCUMENTS

| 4,756,913 A | 7/1988 | Khorkova et al. |
| 2003/0165594 A1 | 9/2003 | Yee et al. |
| 2006/0057247 A1 | 3/2006 | Nguyen et al. |

FOREIGN PATENT DOCUMENTS

| EP | 0 226 035 A1 | 6/1987 |
|---|---|---|
| EP | 1057411 | 12/2000 |
| EP | 1254601 | 11/2002 |
| EP | 1749447 | 2/2007 |
| EP | 2011402 | 1/2009 |
| FI | 120616 | 12/2009 |
| FI | 120616 B | 12/2009 |
| JP | H07-506490 | 7/1995 |
| JP | 2000-270766 | 10/2000 |
| JP | 2008-529547 | 8/2008 |
| JP | 2009-516522 | 4/2009 |
| WO | WO 93/22930 | 11/1993 |
| WO | WO 03/007733 | 1/2003 |
| WO | WO 2004/075644 | 9/2004 |
| WO | WO 2006/087409 | 8/2006 |
| WO | WO 2007/060288 | 5/2007 |
| WO | WO 2007/141385 | 12/2007 |
| WO | WO 2008/071841 | 6/2008 |
| WO | WO 2008/077071 | 6/2008 |
| WO | WO 2009/016257 | 2/2009 |

OTHER PUBLICATIONS

International Search Report for PCT/FI2010/050361 dated Nov. 16, 2010.
Written Opinion of the International Searching Authority dated Nov. 16, 2010.
Search Report for FI 20095500 dated Oct. 27, 2009.
Bonisch et al., "Transglutaminase cross-linking of milk proteins and impact on yoghurt gel properties", International Dairy Journal, vol. 17, Jan. 22, 2007, pp. 1360-1371.
Menendez et al., "Casein gelation under simultaneoua action of transglutaminase and glucono-o-lactone", 2004 Wiley-VCH Verlag GmbH & Co., KGaA, Weinheim, Nahrung Food 48 (2004). No. 3, pp. 165-168.
Eissa et al., "Polymerization and Gelation of Whey Protein Isolates at Low pH Using Transglutaminase Enzyme", Department of Chemical Engineering, North Carolina University, Raleigh, North Carolina, 2004 American Chemical Society, pp. 4456-4464.
Schorsch et al., Cross-linking casein micelles by a microbial transglutaminase: influence of cross-links in acid-induced gelation, International Dairy Journal 10 (2000), pp. 529-539.
Schorsch et al., Cross-linking casein micelles by a microbial transglutaminase conditions for formation of transglutaminase-induced gels, International Dairy Journal 10 (2000) pp. 519-528.
Myllarinen, et al., "Effect of transglutaminase on rheological properties and microstructure of chemically acidified sodium caseinate gels", International Dairy Journal 17 (2007) pp. 800-807.
Vasbinder et al., "Gelation Mechanism of Milk as Influenced by Temperature and pH; Studied by the Use of Transglutaminase Cross-Linked Casein Micelles", J. Dairy Sci, 86; pp. 1556-1563.
Lorenzen et al., "Effect of enzymatic cross-linking of milk proteins on functiona; properties of set-style yoghurt", International Journal of Dairy Technology, Aug. 2002, vol. 55, No. 3, pp. 152-158.
Japanese Office Action issued for Japanese Patent Application No. 2012-509068, dated Apr. 1, 2014 (with English Translation).
Aboumahmoud et al., Crosslinking of Whey Protein by Transglutaminase, J. Dairy Sci. 73:256-263 (1990).

*Primary Examiner* — Leslie Wong

(74) *Attorney, Agent, or Firm* — Nixon & Vanderhye P.C.

(57) ABSTRACT

The invention relates to a low-energy, low-fat or fat-free, high-protein soured or unsoured product prepared by means of a crosslinking enzyme, and to a process for the preparation thereof.

36 Claims, No Drawings

PRODUCT AND PROCESS FOR ITS PREPARATION

This application is the U.S. national phase of International Application No. PCT/FI2010/050361 filed 4 May 2010 which designated the U.S. and claims priority to FI 20095500 filed 4 May 2009, the entire contents of each of which are hereby incorporated by reference.

FIELD OF THE INVENTION

The invention relates to a low-energy, low-fat or fat-free, high-protein, optionally soured product prepared by means of a cross-linking enzyme, and to a process for its preparation. By means of the process of the invention, it is possible to reduce the energy content of the product to be prepared in a cost-effective manner.

BACKGROUND OF THE INVENTION

There are no completely carbohydrate-free and fat-free sour milk products in the market at this moment. There is a great interest in and a need and demand for extremely low-energy food products, light products and weight-control products.

In the preparation of sour milk products, it is typical that starter is added to homogenized, highly heat-treated milk, which, as it sours the milk, provides it with the structure and taste properties typical of the product. As a result of heating, some of the whey proteins of the milk are denatured.

Publication WO 2004/075644 (HP Hood LLC) describes a reduced carbohydrate microbiologically soured dairy product and a process for manufacturing it. An unflavoured soured milk product contains 2.21 to 3.09% carbohydrates, 3.98 to 4.86% protein and 1.33 to 2.20% fat. A flavoured soured product, in turn, contains 3.10 to 3.97% carbohydrates, 0.44 to 1.32% fat and 3.98 to 4.86% protein.

Publication US 2006/0057247 (Ngyen et al.) relates to a process for producing a microbiologically soured dairy product, which contains a small amount of added carbohydrates, from ultrafiltered milk and to a soured dairy product, which contains less than 4.9% carbohydrates and has a viscosity of 900 to 1 600 mPas and a pH of 4.1 to 4.5.

A problem with the products described in these publications is, however, the fact that they contain a great deal of carbohydrates and are, thus, not low-energy products. The maximum carbohydrate contents given to the products are close to the normal carbohydrate content of milk, that is, approximately 4.9%.

Control of the preparation of microbiologically soured low-energy products and the adjustment and maintenance of conditions, such as pH, temperature and time, is problematic, arduous and difficult to manage. In addition, the organoleptic properties of the products are sensitive to disturbances caused by changes in conditions. The preparation of extremely low-energy soured products, especially those from which carbohydrates are removed, is difficult to do with starters, because starter bacteria do not proliferate and acid does not form without adding sugar. Additional costs then arise from raw materials, for instance. In addition, the preparation process and product are more and more difficult to control when a carbohydrate-free, extremely low-energy product is prepared. It is known in the field to add a cross-linking enzyme to the protein source to minimize structural problems. A problem then arises that the processes and their control are further complicated and become more difficult as more preparation steps are added. Thus, simple product formulations and cost-effective preparation processes are needed to control the problems, such as post-souring and structural problems like a powdery structure, caused by the generally known processes to the products.

In the preparation of sour products, chemical souring with for instance glucono-delta-lactone, lactic acid, hydrochloric acid, citric acid, or a combination of different acids is a known alternative for microbiological souring with starters. For instance Schorsch, C. et al. [Int Dairy J 10 (2000), 519-528] and Myllärinen, P. et al. [Int Dairy J, 17 (2007) 800-807] disclose that milk sours chemically by adding glucono-delta-lactone (GDL), such as bacteria producing lactic acid, depending on the souring conditions. Schorsch, C. et al. describe the preparation of casein gel from ultrafiltered calcium-phoso-caseinate by treating it with a cross-linking enzyme, transglutaminase. In publication Int Dairy J 10 (2000) 529-539 (Schorsch, C. et al.), in turn, casein gel is prepared from ultrafiltered calcium-phoso-caseinate by treating it with a cross-linking enzyme and souring it chemically with glucono-delta-lactone (GDL). Myllärinen, P. et al. describe the preparation of milk protein from sodium caseinate or acid casein by chemical souring with GDL and adding treatment with a cross-linking enzyme to the souring. Menéndez, O. et al. (Nahrung/Food 48(3) (2004)165-168) describe the preparation of milk protein from acid-precipitated casein by simultaneous transglutaminase and glucono-delta-lactone treatment. In publication J Agric Food Chem 52 (2004) 4456-4464, (Eissa, A. S., et al.), whey protein is treated at a low pH with a transglutaminase enzyme, and in publication J Dairy Sci 86 (2003) 1556-1563 (Vasbinder, A. J., at al.), solutions made from skimmed milk powder and whey protein-free milk powder were treated with transglutaminase and GDL or D-gluconic acid.

In said publications, the described processes and the raw materials used in them are, however, not industrially applicable but only suitable for research use.

Patent publication FI 20055076 (Valio Oy) describes a low-energy skimmed milk beverage rich in added calcium and containing a low-energy milk base of skimmed milk or whey protein solution or a combination thereof and from which carbohydrates have been removed either entirely or partly, and a process for preparing the same. The energy content of the product is at most 20 kcal/100 g.

Publication WO 2009/016257 relates to a process for producing an acidified milk drink and publication WO 2007060288, in turn, relates to a method of manufacturing soured dairy products. The protein contents of the raw materials used in these processes are in the range of about 30 w-% to about 42 w-% of the dry matter.

Today, retail and consumers require products that contain less energy and are structurally pleasing. It is thus desirable to provide and develop natural processes which are more efficient than before and which ensure the consumer-pleasing organoleptic properties of extremely low-energy products and the preservation of the structure of the product during transportation and even long-term storage.

It has now unexpectedly been found that it is possible to produce from a milk protein raw material having a standardized protein, fat and carbohydrate content extremely low-energy, either unsoured, that is, neutral, or soured milk products that are flawless and/or excellent in structure and taste without any additional costs.

BRIEF DESCRIPTION OF THE INVENTION

The invention relates to a low-energy, low-fat or fat-free, high-protein milk product, and to a process for its preparation by using a cross-linking enzyme. The invention provides for use a new process for the modification and stabilization of the structure of extremely low-energy soured and/or neutral milk products. The process is simple, economical, and industrially applicable in large scale, it does not cause additional costs and advantageously reduces manufacturing costs.

It is very challenging to produce a low-energy product that is flawless in taste and structure and has an energy content of at most 20 kcal/100 g and corresponds to the preferences of consumers in taste and structure. Adding raw materials, such as fibre, to the product increases the challenge and may require additional investments. It has now been unexpectedly found that by using a milk protein fraction having a standardized protein, fat and carbohydrate content, which is optionally evaporated, condensed and/or enzyme-processed with lactase, optionally by heat-treatment and/or microfiltration and by further modifying the milk protein fraction with a cross-linking enzyme and adding thereto at least one mineral, sweetener and/or fibre and at least one flavouring agent, and optionally souring, it is possible to produce extremely low-energy milk products having an excellent taste and structure in a simple and economical manner without any additional costs.

The process of the invention is suitable for the production of soured and/or unsoured low-energy products having excellent taste and structure. By means of the invention, it is also possible to reduce the fat content of the product and/or maximize its protein content. The product of the invention is characterised in that its protein content is more than 40%, fat content less than 10% and carbohydrate content less than 15% of the dry matter.

The object of the invention is achieved with a product and process that are characterised by what is stated in the independent claims. Preferred embodiments of the invention are disclosed in the dependent claims.

DETAILED DESCRIPTION OF THE INVENTION

The invention relates to a low-energy, low-fat or fat-free, high-protein product, and to a process for its preparation by means of a cross-linking enzyme. Typical adjectives describing structural defects associated with low-energy milk products are flaky, lumpy, grit-like and wheying, for instance. In known processes, problems related to the production and storage of low-energy soured products are, among others, associated with non-homogeneity of the product and whey separation in the product during storage. Thus, the present invention offers a solution to avoiding structural defects in low-energy products, which have shown to be problematic. In addition, by means of the process of the invention, it is possible to reduce the energy content of the product.

The present invention offers a new solution to avoiding structural flaws in the preparation of low-energy products, which have shown to be problematic, by using a process which comprises using a milk protein fraction having a standardized protein, fat and carbohydrate content, in which the protein content is approximately 65 to 95%, fat content less than 10% and carbohydrate content less than 15% of the dry matter optionally evaporating, condensing and/or enzyme-treating the milk protein fraction with lactase optionally heat-treating and/or microfiltering the milk protein fraction modifying the protein of the milk protein fraction with a cross-linking enzyme adding at least one mineral, sweetener and/or fibre, when necessary adding at least one flavouring agent, if desired, and/or optionally further-treating and/or packaging the obtained product.

The process optionally also comprises a step, in which the milk protein fraction or obtained mixture and/or mass is soured. The souring may be microbiological and/or chemical. The preparation process of the invention is therefore suitable for producing low-energy unsoured or soured products. Thus, according to an embodiment of the invention, a milk protein fraction having a standardized protein, fat and carbohydrate, especially lactose content is heat-treated, a cross-linking enzyme and, if desired, at least one mineral, sweetener and/or fibre and flavouring agent are added to it and the obtained mass is soured.

The invention also relates to a low-energy product in whose production a milk protein fraction is used having a protein content of 65 to 95%, fat content of less than 10% and carbohydrate content of less than 15% of the dry matter of the product. The invention further relates to a low-energy milk protein product or a low-energy milk protein fraction containing product which has a protein content of more than 40%, fat content of less than 10% and carbohydrate content of less than 15% of the dry matter of the product. According to an embodiment of the invention, the protein content of the milk protein fraction containing product is approximately 40 to 95%, fat content is approximately 0 to 10% and carbohydrate, especially lactose content approximately 0 to 15% of the dry matter of the product. According to another embodiment of the invention, the protein content of the milk protein fraction containing product is 70 to 95%, fat content is 0 to 10% and carbohydrate content is 0 to 15% of the dry matter of the product.

The protein content of the milk protein fraction used in the process of the invention is 65 to 95%, fat content is less than 10% and carbohydrate content is less than 15% of the dry matter. The protein content of the milk protein fraction is preferably 75 to 95%, fat content is less than 5%, more preferably less than 2%, and carbohydrate content is less than 5%, more preferably less than 2%, of the dry matter. An example of the milk protein fraction according to the invention is a fraction having protein content of 75%, lactose content of 1.9% and fat content of 1% of the dry matter. An other example is a milk protein fraction having protein content of 88%, lactose content 2.9% of and fat content 0.7% of the dry matter. The milk protein fraction typically contains whey and casein of milk. The protein composition of cow's milk generally comprises approximately 80% of casein proteins and approximately 20% of whey proteins. The milk protein fraction used in a process of an embodiment of the invention contains essentially the casein and whey proteins contained in the milk raw material. The chemical composition of the milk protein fraction may be for instance as follows: protein 7 to 7.9%, fat 0.09 to 0.14%, lactose 0.07 to 0.37%, ash 1.2 to 1.4% and dry matter 9.0 to 9.3%.

The invention further relates to the use of a milk protein fraction having a protein content of 65 to 95%, fat content of less than 10% and carbohydrate content of less than 15% of the dry matter for the preparation of a low-energy, optionally protein-supplemented, soured or unsoured product.

In connection with the present invention, the milk protein fraction refers to a protein-containing fraction containing milk whey protein and casein and obtainable from milk raw material by different separation techniques, such as, chromatographic or membrane techniques or combinations thereof. The milk protein fraction may also contain milk minerals. The milk raw material may be milk, whey and combinations of milk and whey as such or as concentrate. The milk raw material may originate from a cow, sheep, goat, camel, mare or any other animal that produces milk suitable for human consumption. Fat and carbohydrate are removed from the milk raw material by utilising different separation techniques. The separation technique may be chromatographic separation and/or one or more membrane techniques, such as ultrafiltration (UF retentate, UF concentrate), microfiltration (MF retentate), nanofiltration (NF retentate) or reverse osmosis (RO retentate). The protein-containing fraction is preferably a chromatographically obtained milk protein fraction or combined milk protein and lactose fraction. Chromatographically obtained milk protein fraction contains advantageously also the minerals such as calcium, potassium and sodium. The protein-containing fraction may be supplemented by ingredients used generally in producing milk products and/or whey and milk protein fractions, such as milk protein, whey protein, casein, whey and milk protein fractions, α-lactalbumin, peptides, amino acids, such as lycine. The whey and milk protein fractions may be produced by nanofiltration (NF retentate), for instance.

The milk protein fraction used in the process of the invention may be prepared from the milk raw material by separating fat and separating lactose from skimmed milk chromatographically or using membrane techniques in a manner known per se. The separation of lactose and mineral fraction from milk with a resin balanced with milk minerals is described in patent publication EP 226035, for instance. The process provides the advantage that all ingredients essential for taste can be made to remain in the milk. Chromatographic separation is a process known per se and in industrial use in sugar industry and whey fractionation.

It is also possible to combine vegetable and/or other animal proteins with the milk protein fraction.

In the process of the invention, the milk protein fraction is heat-treated using methods known per se. Useful heat-treatment processes are, among others, pasteurisation, high-pasteurisation, thermisation, UHT treatment and ESL treatment. Examples of suitable heat-treatments include heating at 80-90° C. for 15 seconds to 10 minutes, UHT treatment at 120-150° C. for 1 to 6 seconds and ESL treatment at 135° C. for 0.5 seconds. The heat-treatment may also be performed in several steps. Thus, according to an embodiment of the invention, the milk protein fraction is heat-treated, after which it is processed with a cross-linking enzyme and then heat-treated again.

The protein of the milk protein fraction is modified with a cross-linking enzyme, such as transglutaminase and/or tyrosinase. Amino acids of animal and vegetable proteins may, as known, be cross-linked with enzymes, such as transglutaminase (EC 2.3.2.13). The formed covalent links endure well different process conditions, such as heating and mixing. Of milk proteins, caseins and κ-casein in particular are the best substrate for transglutaminase. β-casein, too, is rich in glutamine and lysine that the enzyme links together.

There are several different commercially available transglutaminase enzyme preparations that are suitable for use in the process of the invention. These include Activa®YG (Ajinomoto, Japan) and Activa®MP (Ajinomoto, Japan) and Yiming-TG (Miming Fine Chemicals Co., Ltd., China). Optimum conditions depend on the used enzyme and they can be obtained from the manufacturers of the commercial enzymes.

The milk protein fraction may be processed with a cross-linking enzyme without a heat-treatment before it. However, a considerable number of cross-links are formed after heat-treatment and the proteins even polymerise.

The thickness of the structure of the product being prepared with the process of the invention is adjusted by varying the dosage of the cross-linking enzymes. The product may be a "set-type" shearing and spoonable product or a stirred and spoonable product, a drinkable product, or a UHT product, or spray or freeze dried powder and/or a product reconstituted from it. For instance the essential amino acids in the milk proteins are nutritionally in a well-absorbing form in the product.

In the process of the invention, the milk protein fraction may also be treated with a lactase enzyme. The lactase treatment may be done simultaneously with the treatment with a cross-linking enzyme. On the other hand, the lactase treatment may also be done separately from the treatment with a cross-linking enzyme, either before or after the treatment with a cross-linking enzyme. Thus, according to one embodiment of the invention, a milk protein fraction having a standardized protein, fat and carbohydrate content is heat-treated, a cross-linking enzyme, lactase enzyme and, if desired, at least one mineral, sweetener and/or fibre and flavouring agent are added to it and the obtained mixture is soured.

There are several different commercially available lactase enzymes (13-D-galactosidases) that are suitable for use in the process of the invention. These include for instance enzymes produced with the *Kluyveromyces fragilis* strain, such as HA lactase (Chr. Hansen A/S, Denmark), or enzymes produced with the *Kluyveromyces lactis* strain, such as Validase (Valley Research Inc., USA), Maxilact L2000 lactase (DSM, Holland) and Godo YNL (Godo Shusei Company, Japan). Optimum hydrolysis conditions depend on the used enzyme and they can be obtained from the manufacturers of the commercial enzymes.

In the process of the invention, the optionally added mineral(s), sweetener(s) and/of fibre(s) may be added separately or as a mineral-sweetener-fibre mixture, the mixture containing at least one mineral, at least one sweetener and/or at least one fibre.

The added minerals may be calcium, potassium, magnesium and/or iron, for instance. Studies show that calcium has a positive effect on weight control. Calcium may be in different forms in the mixture, for instance as Ca-lactate-gluconate, milk calcium, Ca-gluconate, Ca-lactate, Ca-citrate, Ca-carbonate or as some other soluble calcium salt or mixture thereof. The product of the invention may contain calcium in an amount of 100 to 240 mg/100 g product. Correspondingly, the other minerals may be soluble minerals or mixtures thereof. The minerals are preferably added as a milk minerals (whey minerals), for instance. The mineral is preferably added after the heat-treatment of the milk protein fraction.

Possible added sweeteners include polyols, such as xylitol, sorbitol, maltitol and/or glycerol, aspartame, acesulfame-K, sucralose, fructose, saccharine, cyclamate, tagatose, stevia, neotame or thaumatin or mixtures thereof. The sweetener may be added before a possible heat-treatment of the milk protein fraction or after it.

The added fibre may be a soluble and/or insoluble fibre or a mixture thereof. Suitable fibres include polydextrose, other synthetic fibres, inulin, fructo- and galacto-oligosaccharides, pectin, beta-glucan, guar gum, xanthan gum, gellan gum, arabic gum, carrageenan and locust bean gum. Other suitable fibres are for instance dried berry seeds and peels/skins (blackcurrant, blueberry, bilberry, buckthorn, aronia berry, rosehip, cranberry, lingonberry, etc.), starch (amylose-rich Hi-maize starch) and cereal fibres (e.g. oat beta-glucan). The fibre may be added before a possible heat-treatment of the milk protein fraction or mass or after it.

The minerals, sweeteners and/or fibres or their mixtures to be added are heat-treated if desired or required in methods known per se. Examples of heat-treatments of the invention include heating at 80-90° C. for 15 seconds to 10 minutes, UHT treatment at 120-150° C. for 1 to 6 seconds and ESL treatment at 135° C. for 0.5 seconds.

It is also possible to add flavours to the product of the invention. Natural or nature-identical flavours (e.g. lemon, blackcurrant, peppermint) provide the product with various good and tasty flavour combinations and, thus, also further improve the organoleptic properties of the product.

In the process of the invention, the treatment with a cross-linking enzyme may be done before the optional lactase enzyme treatment, simultaneously with it or after the lactase treatment. Consequently, according to an embodiment of the invention, the lactase treatment is done before the treatment with a cross-linking enzyme, whereby the milk protein fraction is treated with a lactase enzyme, heat-treated and cooled, the cross-linking enzyme is added, the mineral-sweetener-fibre mixture, which has as necessary been separately heat-treated, is added, the flavours are added, the starter is added, the mass is mixed, packaged and allowed to sour.

In the process of the invention, the treatment with a cross-linking enzyme may be done before the optional souring, simultaneously with it or after the souring. Thus, according to an embodiment of the invention, a milk protein fraction having a standardized protein, fat and carbohydrate content is produced, it is heat-treated, a possibly separately heat-treated mineral-sweetener-fibre mixture and/or flavours are added, a starter and cross-linking enzyme are added, whereby the protein in the milk protein fraction is modified with the cross-linking enzyme simultaneously with souring.

The souring is done microbiologically and/or chemically. Microbiological souring may be performed utilising starter cultures as souring agents and techniques known in the field. Chemical souring is done by adding a chemical starter, organic acids and/or inorganic acids as a souring agent. Examples of these include glucono-delta-lactone (GDL), calcium lactate, citric acid, lactic acid. Natural acids from berries and fruit, such as the benzoic acid of lingonberry, may also be used in souring. When using microbiological souring, it is necessary to make sure that the conditions required by the used starter bacteria are implemented in terms of nutrients, pH and temperature, for instance. According to an embodiment of the invention, the souring is done by adding a chemical starter, organic acids and/or inorganic acids. The acid used in souring is preferably glucono-delta-lactone.

According to an embodiment of the invention, souring is not done, whereby the process of the invention produces a neutral or unsoured product. In this embodiment, the protein content of the milk protein fraction is preferably increased by adding protein supplements used generally in the production of milk products to the milk protein fraction. Further, in this embodiment, rennet is preferably added to the milk protein fraction during the treatment with the cross-linking enzyme. Thus, according to an embodiment of the invention, a milk protein fraction having a standardized protein, fat and carbohydrate content is produced, it is heat-treated, at least one optionally separately heat-treated mineral, sweetener and/or fibre is added, flavours are added, rennet is added, and the protein in the milk protein fraction is modified with a cross-linking enzyme to obtain an unsoured or neutral gel product. The used rennet may be of animal or vegetable origin or microbiologically produced.

According to an embodiment of the invention, the mineral, sweetener and/or fibre or a mixture thereof or alternatively only part of the ingredients and additives of the mixture are added to the enzyme-treated and possibly soured, preferably enzyme-treated and soured, milk protein-based mass. Thus, according to an embodiment of the invention, a milk protein fraction having a standardized protein, fat and carbohydrate content is heat-treated, flavours are added, a starter is added and the protein of the milk protein fraction is modified with a cross-linking enzyme simultaneously with souring, finally at least one mineral, sweetener and/or fibre or a possibly separately heat-treated mixture thereof is added to the soured mass under continuous agitation to obtain a stirred soured milk protein product.

The process of the invention may further contain optional process steps, such as homogenisation. Consequently, according to an embodiment, the milk protein fraction is heat-treated and homogenised, after which it is processed with a cross-linking enzyme, and a separately heat-treated mineral-sweetener-fibre mixture and/or flavours are added to it. The process of the invention may also include as an optional process step a further-processing step, in which the mixture based on a heat- and enzyme-treated milk protein fraction is treated in a manner required by the product being prepared for instance by adding ingredients, mixing, cooling, packaging and/or recovering the product in some other manner characteristic of the product.

In the preparation of the milk protein fraction containing product according to one embodiment of the invention, the milk protein fraction having a protein content in the range of 65 to 95%, fat content less than 10% and carbohydrate content less than 15% of the dry matter is heat-treated, modified with a cross-linking enzyme, soured and packed.

In the preparation of the milk protein fraction containing product according to another embodiment of the invention, the milk protein fraction having a protein content in the range of 65 to 95%, fat content less than 10% and carbohydrate content less than 15% of the dry matter is heat-treated, supplemented with soluble fibre, flavouring agent(s) and sweetener(s), soured and modified with a cross-linking enzyme, and then packed.

The product becomes a probiotic product, when a desired quantity of probiotic bacteria, such as bifido bacteria and/or lactobacilli, are added to it as a starter (seed), whereby their quantity in the product does not essentially change.

Possible other functional supplements are omega-3 fatty acids, chlorophyll, antioxidants and/or water-soluble or fat-soluble vitamins, blood pressure-affecting tripeptides, cholesterol content-affecting sterols and stanols and their esters, and satiation-increasing compounds or compositions, such as food fat compositions having an oil-in-water emulsion structure.

In connection with the present invention, the expression "low-energy" refers to a product having an energy content of at most 20 kcal/100 g. Alternatively, the product of the invention is a protein-supplemented low-energy product, in which case its energy content is at most 40 kcal/100 g of product. The energy content of a protein-supplemented low-energy product originates from protein. An example of such a product is a fat-free soured protein-containing milk protein preparation that is especially well-suited for consumption during an athletic performance or after it.

The expression "extremely low-energy", in turn, refers to a product having an energy content of 12 to 18 kcal/100 g. Thus, the energy content of a sour milk product of the invention is typically less than 20 kcal/100 g of soured milk protein product. The energy content of an extremely low-energy sour milk product of the invention is, in turn, 12 to 18 kcal/100 g of soured milk protein product.

In connection with the present invention, the expression "fat-free" refers to a product that contains fat at most 0.5 g/100 g in solid or 0.5 g/100 ml in liquid foodstuffs. The expression "low-fat", in turn, refers to a product that contains fat at most 3 g/100 g in solid or 1.5 g/100 ml in liquid foodstuffs (1.8 g/100 ml for semi-skimmed milk). Consequently, the low-energy product of the invention is typically low-fat, whereby its fat content is less than 3%, or alternatively fat-free, whereby its fat content is less than 0.5%.

The expression "protein-rich product" refers to a product having a protein content of more than 40%, preferably in the range of 40 to 95%, of the dry matter of the product. According to an embodiment of the invention, the protein content of a protein-rich product is from 65 to 95%.

Typical of a low-energy product of the invention is that the relative protein content of the dry matter is higher than that of known and/or conventional milk-based fresh products. The protein content of a low-energy sour milk product is in general 1 to 10% and typically approximately 2 to 5%. In the process of the invention, it is possible to adjust the protein content of an extremely low-energy liquid product to 2.5 to 7%.

The process of the present invention is suitable for the preparation of all types of unsoured and/or soured milk products and/or fresh products, typically yogurt, fermented milk, villi, sour cream, smetana and quark, cottage cheese, cheese-like products and feta-type cheeses. When soured products are prepared, the enzyme treatment is performed with a cross-linking enzyme and, if necessary, with a lactase enzyme preferably before souring and other appropriate further-processing.

According to an embodiment of the invention, the milk protein fraction may be foamed. The treatment with a cross-linking enzyme is then performed during or after the foaming. If the foamed product is chemically soured, the treatment with a cross-linking enzyme may be done during the chemical souring and foaming.

The process of the invention is simple and suitable for large-scale production.

The process of the present invention may be applied to both batch and continuous production. The process of the invention is preferably done as a batch process.

The following examples describe the performance of the invention, but do not restrict the invention to said product embodiments.

Example 1 "Set Type" Snack

To prepare the snack, milk having a fat content of 1.5% was used, from which fat was separated by separation and lactose by chromatography from skimmed milk. A milk protein fraction having the following composition was obtained: protein 7%, fat 0.09%, lactose 0.18%, ash 1.3%, sodium 0.18%, calcium 230 mg/100 g, dry matter 9.3%.

The milk protein fraction was diluted to 3% with water. The mixture was heated at 80 to 90° C. for 8 to 10 min. Cooled to 25° C. Soluble fibre (polydextrose, Litesse, Danisco A/S) was added to the milk protein fraction. Flavours and sweeteners (aspartame/acesulfame-K) were added. A chemical starter, glucono-delta-lactone (Algol), 1 to 2% of the volume, and a transglutaminase enzyme (Ajinomoto, Japan), 0.3 to 0.6 U/g protein, were added. The mixture was dosed into beakers that were closed with lids. They were let sour for approximately 22 hours at a temperature of 25° C. Cold-stored (+6-8° C.) for 3 weeks.

The obtained product contained 0.05% fat, 3% protein, 0.1% carbohydrates and an extremely small amount of energy (energy content 12 to 13 kcal/100 g).

Alternatively, berries, cereals/grains and fibres were packed separately on the lids of the beakers.

Example 2 "Set Type" Snack—Milk Protein Fraction UF Concentrate

A UF concentrate (protein content approximately 12%, 88% of the dry matter, fat 0.09%, lactose 0.4%, ash 1.2%) made by ultrafiltration was diluted with water to a 3% solution (ash 0.3%). Heated at 80 to 90° C. for 8 to 10 min. Cooled to 25° C. To the diluted UF fraction, 0.5% of milk minerals (Valio Milk Mineral Powder, ash 41%) was added. The ash content of the diluted UF concentrate was then on the same level as the ash content in Example 1. Fibre was added to the protein fraction. Flavouring agents and sweeteners were added. Chemical starter GDL (1 to 2% of the volume) and transglutaminase enzyme (Ajinomoto, Japan), 0.3 to 0.6 U/g per protein, were added. The mixture was dosed into beakers and the lids were sealed. They were let sour for approximately 22 hours at a temperature of 25° C. Cold-stored (+6-8° C.) for 3 weeks.

Alternatively, berries, cereals/grains and fibres were packed separately on the lids of the beakers.

Example 3—Drinkable/Spoonable Snack (Preparation in Yogurt Process)

A milk protein fraction was prepared as in Example 1. Soluble fibre (polydextrose) was added to the milk protein fraction (approximately 7%). The mixture was heated at 80 to 90° C. for 8 to 30 min. Cooled to 42° C. Transglutaminase enzyme (Ajinomoto, Japan) (0.3 to 0.6 U/g protein) was added. Incubated for 2 hours. After this, the mixture (7% protein) was diluted with water so as to obtain the required protein level of 3 to 3.5%, for instance. After this, chemical starter GDL (1 to 2% of the volume) was added. The mixture was let sour for approximately 4 hours or until pH 4.3 to 4.4 was reached. The structure was broken by mixing and the mass was cooled at the same time to a temperature of approximately 20° C. Flavouring agents and sweeteners (aspartame, acesulfame-K) were added. The mixture was dosed into beakers that were closed with lids. Cold-stored (+6-8° C.) for 3 weeks. Alternatively, berries, cereals/grains and fibres were packed separately on the lids of the beakers.

A drinkable yogurt/snack was prepared as described above, but it was mixed more, whereby the viscosity of the obtained product was lower. Otherwise the product had corresponding properties, and there was no detectable flavour defect.

Example 4—Foamed Product

A product according to Example 3 was prepared and foamed at the end of the preparation process and packed into dosage beakers.

Example 5—Drinkable UHT

A milk protein fraction was prepared as in Example 1. Soluble fibre (polydextrose, Litesse, Danisco A/S) was added to the milk protein fraction (approximately 7%). The mixture was heated at 80 to 90° C. for 8 to 30 min. Cooled to 42° C. Transglutaminase enzyme (Ajinomoto, Japan) (0.3 to 0.6 U/g protein) was added. Incubated for 2 hours. The mixture (7% protein) was diluted with water so as to obtain the required protein level of 3 to 3.5%, for instance. After this, chemical starter GDL (Algol) (1 to 2% of the volume) was added. The mixture was let sour for approximately 4 hours or until pH 4.3 to 4.4 was reached. The structure was broken by mixing and the mass was cooled at the same time to a temperature of approximately 20° C. Flavouring agents, sweeteners and other possible agents were added. The mass was heat-treated in a UHT process (141° C., 75 s) and aseptically packed.

The structure of the finished drinkable yogurt was smooth and velvety. During storage, whey did not separate, not even when the yogurt was stored at room temperature for weeks.

Example 6—Drinkable ESL

A product according to Example 5 was prepared with the exception that the milk was sterilised by microfiltration and the finished mass was heat-treated in an ESL process (120 to 135° C., 0.5 to 1 s) and aseptically packed.

Example 7—Powder

A milk protein fraction was prepared as in Example 1. Fibre (polydextrose) was added to the milk protein fraction (approximately 7%). The mixture was heated at 80 to 90° C. for 8 to 30 min. Cooled to 42° C. Transglutaminase enzyme (Ajinomoto, Japan) (0.3 to 0.6 U/g protein) was added. Incubated for 2 hours. The mixture (7% protein) was diluted with water so as to obtain the required protein level of 3 to 3.5%, for instance. After this, chemical starter GDL (1 to 2% of the volume) was added. The mixture was let sour for approximately 4 hours or until pH 4.3 to 4.4 was reached. The structure was broken by stirring and the mass was cooled at the same time to a temperature of approximately 20° C. Flavouring agents and sweeteners were added. For freeze-drying, the mass was frozen on drying trays and dried to powder (water content less than 2%) and packed in water-resistant bags.

Alternatively, the mass was dried by spray drying and packed into sacks. When water was added to the powder, a spoonable or drinkable product was reconstituted from the power.

The invention claimed is:

1. A process for the preparation of a milk protein fraction containing product, wherein the process comprises the following steps
    using a milk protein fraction produced by membrane filtration consisting of ultrafiltration as the sole membrane filtration or by chromatographic separation and having a protein content in the range of 65 to 95%, fat content less than 10% and carbohydrate content less than 15% of the dry matter,
    optionally evaporating, condensing and/or enzyme-treating the milk protein fraction with lactase,
    optionally heat-treating and/or microfiltering,
    modifying the protein of the milk protein fraction with a cross-linking enzyme,
    adding at least one mineral, sweetener and/or fibre, when necessary,
    adding flavouring agents, if desired, and/or
    optionally further-treating and/or packaging the obtained product.

2. The process as claimed in claim 1, further comprising a step in which the milk protein fraction is soured.

3. The process as claimed in claim 2, wherein the milk protein fraction is chemically soured.

4. The process as claimed in claim 2, wherein the treatment with cross-linking enzyme is done before souring, simultaneously with souring or after souring.

5. The process as claimed in claim 1, wherein the lactase treatment is done simultaneously with the treatment with a cross-linking enzyme.

6. The process as claimed in claim 1, further comprising treatment with rennet.

7. The process as claimed in claim 6, wherein the treatment with rennet is done simultaneously with the treatment with a cross-linking enzyme.

8. The process as claimed in claim 1, wherein the protein content of the milk protein fraction is supplemented by adding a protein-rich fraction generally used in the preparation of milk products.

9. The process as claimed in claim 3, wherein the souring is performed by adding a chemical starter, organic acids and/or inorganic acids.

10. The process as claimed in claim 1, wherein at least one mineral, sweetener and/or fibre or a mixture thereof or alternatively only part of the ingredients and additives of the mixture are added into the milk protein fraction or into the enzyme-treated and possibly soured mass.

11. A low-energy unsoured or soured milk protein fraction containing product, which contains energy at most 40 kcal/100 g and which is prepared by a process of claim 1.

12. A low-energy unsoured or soured milk protein fraction containing product, which contains more than 40% protein, less than 10% fat and less than 15% carbohydrate of the dry matter and energy at most 40 kcal/100 g.

13. The product as claimed in claim 12, wherein the product contains 65 to 85% protein, less than 5%, preferably less than 2% fat, and less than 5%, preferably less than 2% carbohydrate of the dry matter.

14. The product as claimed in claim 11, wherein the product is an extremely low-energy, soured milk protein fraction containing product, which contains energy at most 20 kcal/100 g.

15. A method for the preparation of a low-energy, soured or unsoured product utilizing a milk protein fraction produced by membrane filtration consisting of ultrafiltration as the sole membrane filtration or by chromatographic separation and having a protein content of 65 to 95%, fat content of less than 10% and carbohydrate content of less than 15% of the dry matter, as the starting material.

16. The method as claimed in claim 15, wherein the product is chemically soured.

17. The product as claimed in claim 13, wherein the product contains energy at most 20 kcal/100 g.

18. The process as claimed in claim 1, wherein the milk protein fraction is a sole and only source for milk based proteins.

19. The process as claimed in claim 1, wherein the milk protein fraction has the protein content in the range of 75-95%, fat content less than 5% and carbohydrate content less than 5% of the dry matter.

20. The method of claim 15, wherein the milk protein fraction is a sole and only source for milk based proteins.

21. A process for the preparation of a milk protein fraction containing product, wherein the process comprises the following steps
- using, as a sole and only source for milk-based proteins, a milk protein fraction having a protein content in the range of 65 to 95%, fat content less than 10% and carbohydrate content less than 15% of the dry matter,
- optionally evaporating, condensing and/or enzyme-treating the milk protein fraction with lactase,
- optionally heat-treating and/or microfiltering,
- modifying the protein of the milk protein fraction with a cross-linking enzyme,
- adding at least one mineral, sweetener and/or fibre, when necessary,
- adding flavouring agents, if desired, and/or
- optionally further-treating and/or packaging the obtained product.

22. The process as claimed in claim 21, further comprising a step in which the milk protein fraction is soured.

23. The process as claimed in claim 22, wherein the milk protein fraction is chemically soured.

24. The process as claimed in claim 22, wherein the treatment with cross-linking enzyme is done before souring, simultaneously with souring or after souring.

25. The process as claimed in claim 21, wherein the lactase treatment is done simultaneously with the treatment with a cross-linking enzyme.

26. The process as claimed in claim 21, further comprising treatment with rennet.

27. The process as claimed in claim 22, wherein the treatment with rennet is done simultaneously with the treatment with a cross-linking enzyme.

28. The process as claimed in claim 21, wherein the protein content of the milk protein fraction is supplemented by adding a protein-rich fraction generally used in the preparation of milk products.

29. The process as claimed in claim 23, wherein the souring is performed by adding a chemical starter, organic acids and/or inorganic acids.

30. The process as claimed in claim 21, wherein at least one mineral, sweetener and/or fibre or a mixture thereof or alternatively only part of the ingredients and additives of the mixture are added into the milk protein fraction or into the enzyme-treated and possibly soured mass.

31. A low-energy unsoured or soured milk protein fraction containing product, which contains energy at most 40 kcal/100 g which is prepared by a process of claim 21.

32. A method for the preparation of a low-energy soured or unsoured product utilizing, as a starting material, a milk protein fraction, having a protein content of 65 to 95%, fat content of less than 10% and carbohydrate content of less than 15% of the dry matter, as a sole and only source for milk-based proteins.

33. The method as claimed in claim 32, wherein the product is chemically soured.

34. The process as claimed in claim 21, wherein the milk protein fraction is produced by ultrafiltration or chromatographic separation.

35. The process as claimed in claim 21, wherein the milk protein fraction has the protein content in the range of 75-95%, fat content less than 5% and carbohydrate content less than 5% of the dry matter.

36. The method of claim 32, wherein the milk protein fraction is produced by ultrafiltration or chromatographic separation.

* * * * *